United States Patent [19]

Roussel

[11] 4,283,146
[45] Aug. 11, 1981

[54] OPTICAL DETECTOR
[75] Inventor: Philippe Roussel, Thun, Switzerland
[73] Assignee: Lasag S.A., Thun, Switzerland
[21] Appl. No.: 964,884
[22] Filed: Nov. 30, 1978
[51] Int. Cl.³ .................... G01N 21/55; G01B 11/00
[52] U.S. Cl. .................................. 356/445; 356/384; 356/397
[58] Field of Search .............................. 356/445–448, 356/336, 442, 384, 397

[56] References Cited
U.S. PATENT DOCUMENTS
3,016,464 1/1962 Bailey .................................. 356/447

OTHER PUBLICATIONS
NASA Tech. Brief NTN-78/0156, "Optical Proximity Detector", NPO-13306, Caltech/JPL, Pasadena, California.

Van Nostrand's Scientific Encyclopedia's definition of "collimator", Princeton, N.J., Fourth Edition, 1968.

Primary Examiner—John K. Corbin
Assistant Examiner—Bruce Y. Arnold
Attorney, Agent, or Firm—Sherman & Shalloway

[57]     ABSTRACT
An optical detector for the detection of very small objects comprises a first optical system defining an optical path and being operable to transmit electromagnetic radiation onto an object to be detected; a second optical system defining an optical path parallel to said optical path of said first optical system and being operable to receive said electromagnetic radiation after diffusion and reflection by said object; and a converging lens associated in common with said first and second optical systems and arranged such that said optical paths of said first and second optical systems are parallel to and symmetrical about the axis of said converging lens on one side thereof.

23 Claims, 5 Drawing Figures

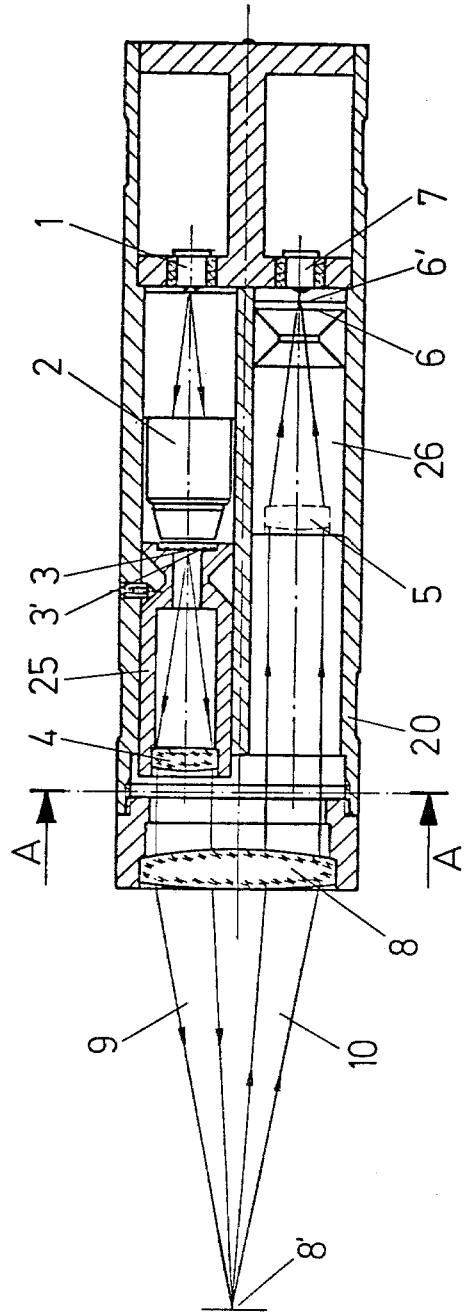
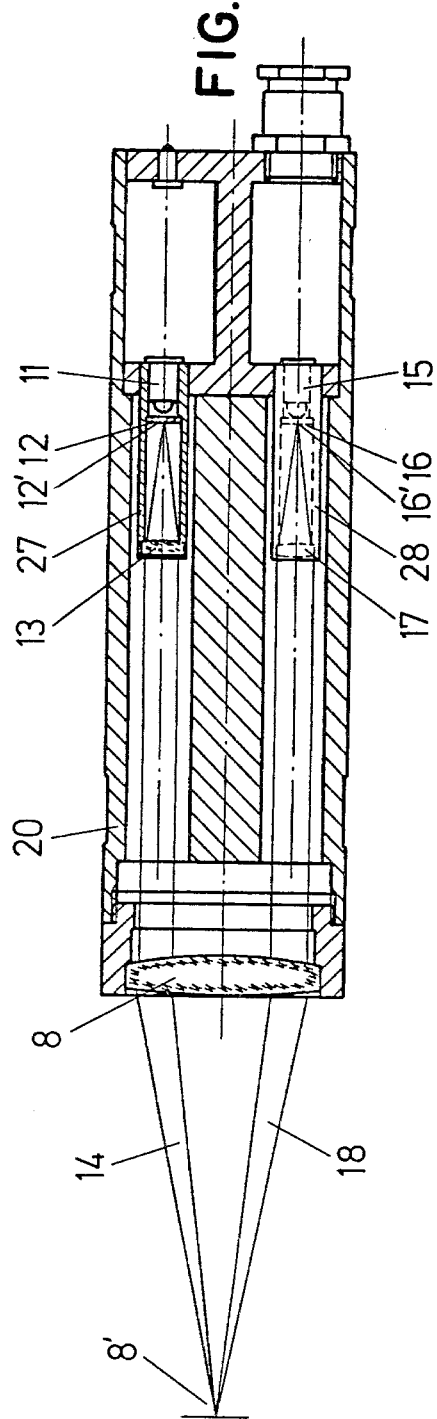

OPTICAL DETECTOR

BACKGROUND OF THE INVENTION

The present invention relates to an optical detector, operating by direct reflection, for detecting presence or absence of an object.

Known detectors, also called proximity detectors, operate either by transmission or by reflection, and are called upon to work equally in one mode or the other.

Transmission detectors perceive the interruption of a light beam by an object to be detected. They necessarily comprise a unit for the transmission of a beam of light rays and a unit for the detection of the beam of light. Such apparatus has a limited application if it is not possible to dispose the two units in a straight line which only the object to be detected can interrupt.

Known reflection-type optical detectors are of two kinds. In both cases, the transmission of a beam of light rays and the detection of the same beam after reflection or diffusion take place by means of members in the same unit. In the first kind, the reflection-type detector can detect the light reflected by an object to be detected and in the second kind they are sensitive to the interruption of the beam reflected by a specially provided reflector. Detectors of this second indirect reflection type have the same disadvantages as those operating by transmission in regard to the interruption of the beam by any object.

Reflection-type optical detectors sensitive to light rays directly reflected by an object to be detected are constructed in various forms. The transmitted beam can be divergent, parallel or convergent. The reflected rays are collected by a second optical system, or by the same optical system as the transmitted rays, in which case they are thereafter separated by a semi-transparent mirror or an apertured mirror for directing them onto a photo-detector.

All these detectors are very severely limited in their performances in the detection of small objects from a great distance. The detector heads must be brought to within a few millimeters of the object to be detected, which is often impossible for reasons of space.

A solution already proposed for overcoming this difficulty is to make use of optical fibres for bringing the light rays into proximity to the object and collecting them. This solution also has its limits. The constructions having the best performance include those which utilise the transmission of a convergent beam and the reception of the rays reflected along a separate optical path. The directions of illumination and observation are at a certain angle. However, the further the zone of detection is from the detector, the larger the detector becomes.

SUMMARY OF THE INVENTION

The present invention has for an object to provide an optical detector operating by direct reflection which is capable of detecting the presence or absence of objects (or holes) in an extremely small volume of space, situated at a great distance (frontal distance) from the detector.

According to the present invention there is provided an optical detector comprising:

a first optical system defining an optical path and being operable to transmit electromagnetic radiation onto an object to be detected;

a second optical system defining an optical path parallel to said optical path of said first optical system and being operable to receive said electromagnetic radiation after diffusion and reflection by said object; and a converging lens associated in common with said first and second optical systems and arranged such that said optical paths of said first and second optical systems are parallel to and symmetrical about the axis of said converging lens on one side thereof.

Advantages of a detector according to the invention will be explained in the course of the following description, which refers to the accompanying figures.

BRIEF DESCRIPTION OF THE DRAWINGS

For a better understanding of the invention and to show how it may be put into effect reference will now be made, by way of example, to the accompanying drawings in which:

FIG. 1 is a longitudinal sectional view of one embodiment of optical detector according to the invention;

FIG. 2 is a longitudinal section along a plane perpendicular to the plane of FIG. 1;

DETAILED DESCRIPTION OF THE DRAWINGS

Figure 3:
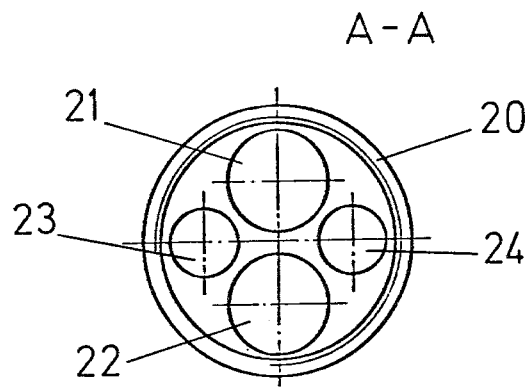
FIG. 3 is a transverse section along the plane A—A of the detector according to FIG. 1.

In FIG. 1 an optical system for the transmission of electromagnetic radiation in the form of light rays comprises a light emiting diode (LED) 1, a condenser 2, a diaphragm 3, and a lens focused on a hole 3' of the diaphragm 3.

An optical system for receiving light rays comprises, in the illustrated case, a lens 5 focused on a hole 6' of a diaphragm 6, behind which there is situated a light-ray detector such as a photo-transistor 7, a photo-resistor, a thermo-couple or a differential diode.

A lens 8 is common to these two optical systems, which are parallel to one another and disposed symmetrically about the optical axis of the lens 8 and on the same side of the lens 8.

The principle of operation is as follows: The rays emitted by the emitting diode 1 are collected by the condenser 2 and focused on the hole 3' of the diaphragm 3. The illuminating light beam 9 is converted into a parallel beam by means of the converging lens 4, whereafter it is focused at the focus 8' of the common lens 8. When a plane surface perpendicular to the optical axis is situated exactly at the focus 8' of the common lens 8, an image of the hole 3' is materialised at 8'. This image gives rise to an observation light beam 10, which is formed of the rays reflected or diffused by the object at the focus 8'. The observation beam 10 converges on the hole 6' of the diaphragm 6 after having passed through the lenses 8 and 5. The photo-transistor behind the hole 6' collects the luminous energy of the observation beam and signals, by means of an associated electronic detection circuit, the presence of an object at the focus 8' of the common lens 8.

Should an object other than that to be detected interrupt the illumination beam elsewhere than at the focus 8' (either in front of or behind the focus 8'), the observation beam would then not become focused on the hole 6' of the diaphragm 6, but would pass, due to the phenomenon of parallax, onto the diaphragm 6 itself. No signal is then picked-up by the photo-transistor 7.

The major advantages of the illustrated and described presence detector will be obvious from the foregoing description.

The detector is capable of detecting the presence or absence of bodies at a great distance and in an extremely small volume of space. In fact, the distance is determined by the focal length of the common lens 8.

The detector is capable of detecting small bodies, that is to say its observation volume is very small. The image of the hole 3' at the focus 8' can be dimensioned by the choice of a diaphragm 3 of which the hole 3' is larger or smaller depending upon the desired sensitivity. In addition, it is not necessary for the entire image to be diffused by an object, but it is sufficient merely for a part of the image to set up the observation beam 10, the detector being capable of detecting the presence of a metal wire having a diameter of 0.1 mm to 25 cm, for example.

The optical presence detector is capable of detecting the presence or absence of a protuberance situated on a background of like appearance and having like surface orientation, since it is designed to detect objects in a small volume on the focus 8' of the common lens 8.

Therefore, depending upon the dimensions of objects and the characteristics of the device employed, it is not necessary to take any precautions in regard to the reflectivity of obstacles situated behind the object to be detached.

The improvements hereinafter described have been made in the illustrated and described presence detector:

A first improvement involves the choice of the light source. It is preferably applicable to an electroluminescent LED whose luminous emission can be modulated at high frequency and which does not give rise to any thermal problems such as arise in filament or arc lamps. The choice of the LED will be adapted to the use of the detector. In industry, the detector will generally be required to detect metal objects, in which case the LED will preferably operate by emission in the infra-red region, because at this wavelength metals exhibit very similar reflectivity regardless of their composition. Moreover, the surface state has less effect on the reflectivity of longer waves than in the case of shorter wavelengths.

The electronic control circuit of the LED 1 will preferably comprise a negative-temperature-coefficient resistance in order to regularise the transmission of infra-red light as a function of the temperature of the LED 1.

A second improvement is tied to the first and consists in rendering visible the focal point 8' of the infra-red detection beam. The means chosen consists in providing in the detector unit itself at least one additional light source operating in the visible range. The manner in which this improvement is applied is illustrated in FIG. 2, which is a longitudinal section along a plane at 90° to the section of FIG. 1. FIG. 3, which is a transverse section through the detector, illustrates the relative locations of the optical systems of FIGS. 1 and 2.

In FIG. 2, there will be seen a first optical system for the marking of the focus 8'. Its optical axis is parallel to the axis of the lens 8 and therefore also parallel to the axes of the optical system for the transmission of the infra-red rays and of the optical system for the reception of the rays. This first optical marking system comprises a photo-diode operating in the visible range, or marking photo-diode 11, a diaphragm 12 with a centered hole 12', a converging lens 13 having its focus 13' on the hole 12' and sending the image from this hole to infinity. This parallel marking beam 14 is focused at 8' by the lens 8.

This first marking optical system can be duplicated by a second identical system consisting of elements 15 to 18, and the focus 8' of the converging lens 8 is then indicated with precision by the superposition of the two images of the holes 12' and 16'.

A third improvement involves the practical construction of the detector. By virtue of the similarity of the optical transmission and observation systems on the one hand, and of the optical marking systems on the other hand, it is possible to envisage designing the optical detector as a whole as an assemblage of modules, as illustrated in FIGS. 1 and 2. FIG. 3 shows that in a basic element consisting of a cylinder 20 there are formed four cylindrical holes 21, 22, 23 and 24 situated with axial symmetry about the axis of the cylinder 20. Four modular elements 25, 26, 27 and 28 of tubular form are introduced therein, comprising respectively the converging lenses 4, 5, 13 or 17 and the diaphragm 3, 6, 12 or 16, of which the central hole is located at the focus of the associated lens. The modular elements 25 and 26 on the one hand, and 27 and 28 on the other hand, are identical. Also they could, strictly speaking, all be identical to one another. The diaphragms 3, 6, 12 and 16 could be made in order to permit rapid change of the aperture, by being demountable.

This arrangement permits rational production and accelerated assembly of the detector.

The converging lens 8 is readily interchangeable, for example by unscrewing, so that the detection distance can readily be modified. It will also be observed that the mechanical axis of the base cylinder 20 is identical with the optical axis of the lens 8. This arrangement facilitates the positioning of the detector and its aiming onto the object to be detected, especially if, in addition, the cylinder 20 is formed with grooves to enable it to be fixed and centered.

A fourth improvement involves the control of the light sources. As already mentioned in the foregoing, the infra-red luminous emission of the LED 1 is modulated and the signal of the photo-transistor 7 is filtered with a narrow band to this same frequency in order to eliminate as far as possible stray light.

The diodes 11 and 15 can be continuously controlled.

A fifth improvement of the detector involves the choice of the receiver of the diffused or reflected beams.

The range of available means comprises thermo-receivers, photo-resistors, photo-transistors and the like. Having regard to the wavelength and the modulation frequency, preference is given to a photo-transistor in Darlington arrangement.

In place of a receiver having a single sensitive zone, it is possible to envisage a receiver having two sensitive zones, such as a differential diode. Such a receiver makes it possible to widen the field of application of the detector.

Let it be imagined that the object whose presence it is desired to detect is situated at a distance greater than the focal length of the detector. As the object approaches the detector, the observation light beam 10 gives rise to a luminous spot which shifts along a straight line on the diaphragm 6, intercepts the hole 6' at the instant when the object is located at the focus 8' and moves away again.

A single-zone receiver emits a signal corresponding to the luminous itensity which it detects, which signal is a maximum when the object is located exactly at the focus 8' of the lens 8.

A two-zone receiver, in which the demarcation between the two zones is a line centered on the hole 6' and not parallel, preferably perpendicular, to the line described by the luminous spot on the diaphragm 6, also makes it possible to indicate whether the object is located in front of or behind the focus 8'. The signals of the two zones are identical when the object is exactly at the focus 8'.

Figure 5:
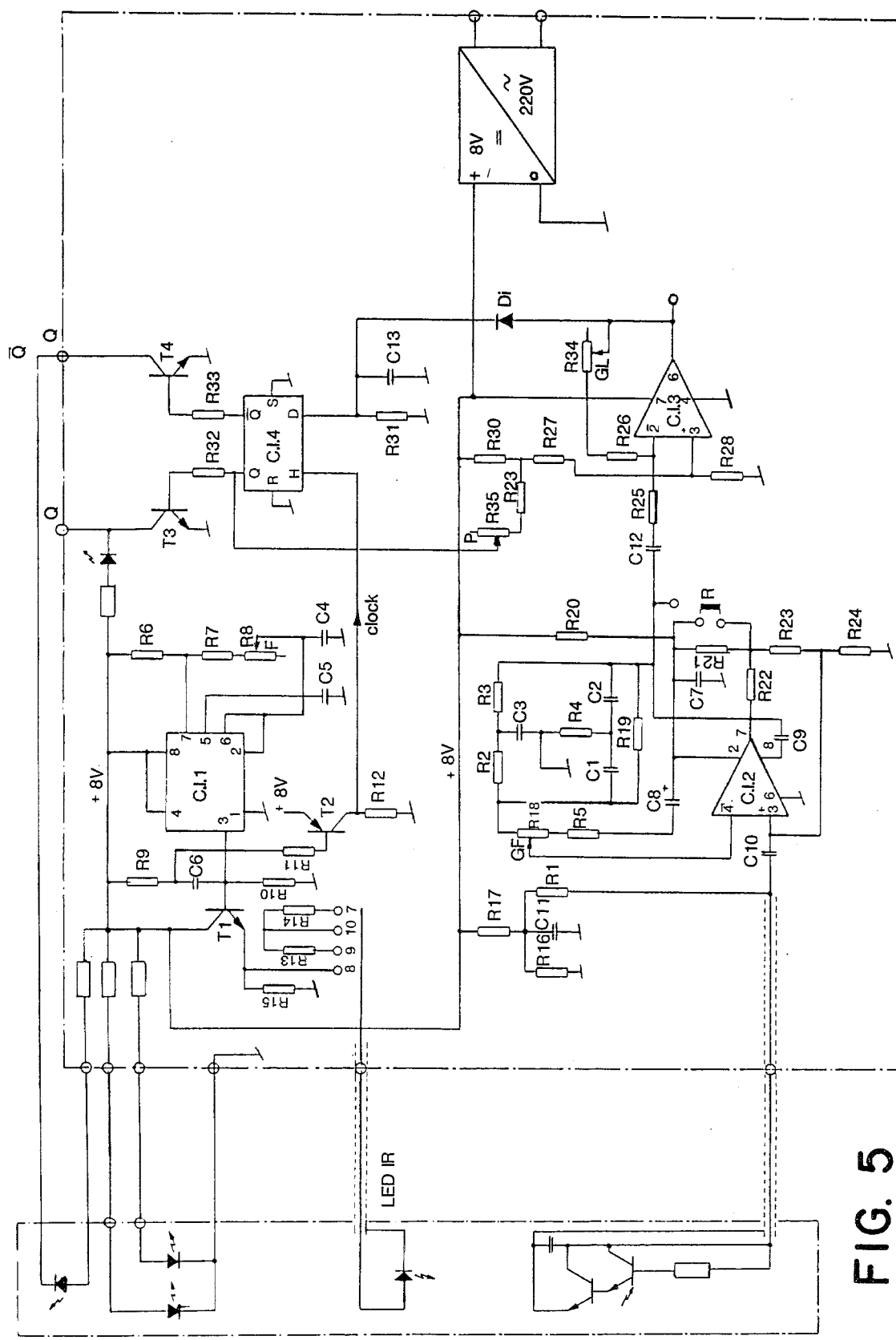
FIG. 5 illustrates in greater detail the electronic circuit of FIG. 4.

A sixth improvement involves the construction of the electronic control and detection circuit illustrated by way of example in the accompanying FIG. 5. The modulation frequency is optimised so as to obtain a maximum gain of the signal of the receiver and, depending upon the components chosen, it is located between 2 and 3 kHz. The measuring time is very short in relation to the time between each measurement (about 0.50%o), whereby the system is rendered insensitive to industrial interference.

Figure 4:
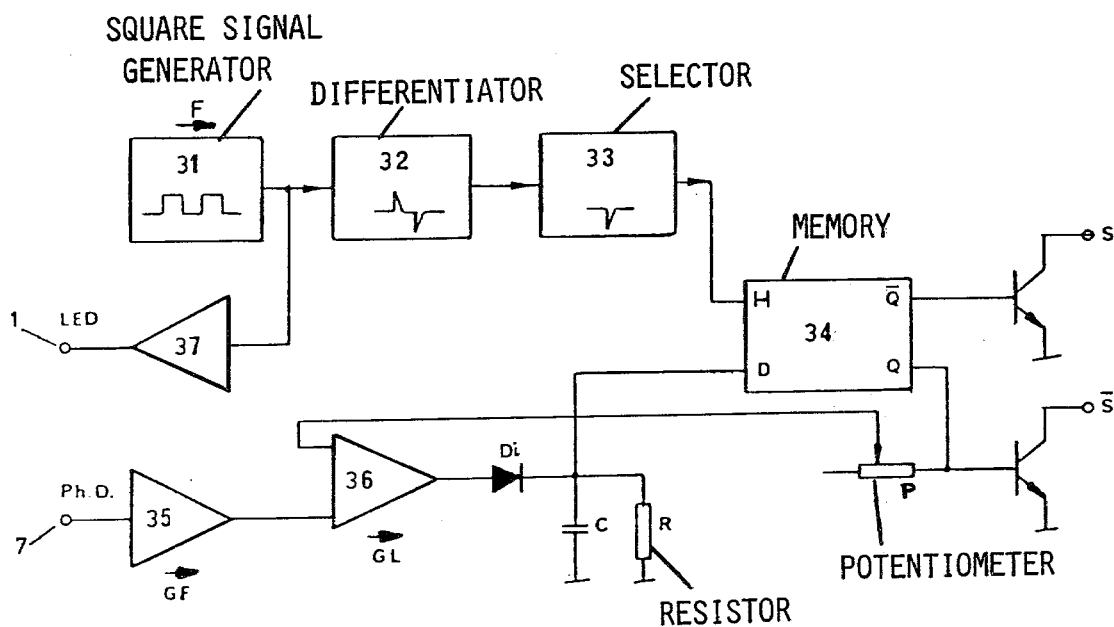
FIG. 4 is the basic diagram of the control and detection circuit of the detector according to FIGS. 1 to 3.

The operating principle illustrated in FIG. 4 is the following. A square-signal generator 31 sends pulses to the input of an amplifier 37 which supplies at its output the current necessary for the feeding of the LED. The pulses from the generator 31 are directed at the same time onto a differentiator 32, whereafter a selector 33 transmits at its output a brief pulse to a memory 34 at its clock input H.

On the other hand, the signal collected at the output of the receiver 7 is applied to the input of a selective amplifier 35. The gain of the latter is adjusted by a selective negative-feedback circuit incorporating a double-T filter. This first amplifier therefore has considerable gain for the modulated frequency, but low gain for the other frequencies. A feedback circuit is incorporated to increase the selectivity of the filter. The modulated signal thereafter enters an amplifier 36. The gain of the latter is adjustable and is not selective. The output voltage is a continuous voltage modulted by the input signal. This continuous voltage determines a threshold which can be adjusted by a potentiometer P connected to the memory 34. The modulated continuous signal passes through a diode Di and charges a capacitor C. During the negative half-cycles, C discharges partially into a parallel resistor R. There is found at the terminals of C a continuous sawtooth voltage. This signal is applied to the input D of the memory 34.

Thus, at each end of a modulated light impulse a clock pulse is applied to the input H of the memory 34. This pulse transfers the logic state from the input D to the output Q or $\overline{Q}$ only if a change of state has occured at the input D. The outputs S and $\overline{S}$ make it possible to have available the logic signal by way of an open-collector transistor adaptable to various integrated logic families (for example, TTL, HTL and C Mos circuits) or electromagnetic relays.

The electronic control and detection circuit is preferably mounted on a standardised plug board. It is connected to the presence detector by the various connecting means illustrated in FIG. 5. One of the connecting means shown in FIG. 5 connects a visual display diode to the output $\overline{Q}$. This visual display diode may be a simple red LED mounted on the detector, which is constantly supplied except at the instant of detection of an object and which serves above all to signal the operation of the presence detector.

A complementary-function diode mounted on the board and connected to Q is shown by way of indication in FIG. 5. This diode assists in effecting the adjustment of the detection threshold by means of the potentiometer P.

The electronic circuit therefore makes it possible to adjust the gain and the switching threshold as a function of the conditions under which the presence detector is used. These conditions of use may vary with the detection distance given by the focal length of the lens 8, with the magnitudes of the apertures of the diaphragms of the optical illumination and observation systems, and with the nature of the object to be detected, i.e. its material, colour, surface state and dimensions, as also with the purpose for which the apparatus is employed.

The principal application of the detector is the detection of the presence or absence of objects (or holes) in a limited zone of space and it lends itself above all to the detection of small objects at a particular distance. Nevertheless, by virtue of its properties, its application may also extend to the following fields:

detection of colours, since it is sensitive to variations of reflectivity of the surface;

detection under special conditions, for example through a port hole;

measurement or monitoring of the angular orientation of the surface by prior grading of the signal at the output of the amplifier 36 as a function of the inclination of the surface in relation to the axis of the detector;

distance measurement within the limited zone of detection of objects, also by prior grading of the signal 36 as a function of the distance from the focus 8' of the lens 8; when the receiver is a differential diode, the distance measurement takes place unequivocally with regard to the signal on either side of the focus 8';

precise range finding: automatic range correction, use as micro-switch, etc.

The presence detector and its associated electronic circuit are preferably constructed as illustrated and described by way of example in the foregoing, but the scope of the invention is in no way limited to this embodiment or to the fields of application referred to.

I claim:

1. An optical detector for the detection of very small objects comprising:
   (a) a first optical system defining an optical path and being operable to transmit electromagnetic radiation;
   (b) a second optical system defining an optical path parallel to said optical path of said first optical system and being operable to receive said electromagnetic radiation after diffusion by an object; and
   (c) a converging lens associated in common with said first and second optical systems and arranged such that said optical paths of said first and second optical systems are parallel to and symmetrical about the axis of said converging lens on one side thereof, wherein
   (d) said first optical system comprises means for transmitting said electromagnetic radiation to said converging lens in a parallel beam, said means for transmitting said electromagnetic radiation comprising a positive lens preceded in said first optical system by a source of said electromagnetic radiation, a condenser for collecting said electromagnetic radiation, and interchangeable diaphragms, each diaphragm having a hole of a different size whose image is transmitted by said electromagnetic radiation to the focal point of said positive lens, said hole being situated at the focus of said condenser.

2. An optical detector as claimed in claim 1, further comprising an electronic system for control of transmission and reception by said first and second optical systems respectively, said electronic system being operable to modulate the electromagnetic radiation from said first optical system.

3. An optical detector as claimed in claim 2, wherein said electronic system comprises a selective amplifier for the signal from said second optical system, succeeded by a device for recognising a detection threshold of the amplified signal, there also being a means for adjusting the gain of said selective amplifier and a means for adjusting said detection threshold in order to enable the sensitivity of the optical detector to be adjusted.

4. An optical detector as claimed in claim 3, and comprising at least one optical means for signalling crossing of said detection threshold.

5. An optical detector as claimed in claim 4, wherein said optical means is an LED.

6. An optical detector as claimed in claim 1, wherein said first optical system is operable to transmit electromagnetic radiation in the infra-red range.

7. An optical detector as claimed in claim 1, wherein said second optical system comprises an electromagnetic radiation detector preceded by a diaphragm formed with a hole and a positive lens positioned with a focal point at said hole.

8. An optical detector as claimed in claim 7, wherein said electromagnetic radiation detector comprises a photo-transistor in Darlington arrangement.

9. An optical detector as claimed in claim 7, wherein said electromagnetic radiation detector comprises a differential diode.

10. An optical detector as claimed in claim 1, wherein an assembly of modular optical systems is provided in a cylindrical base element which has a geometrical axis coincident with said axis of said converging lens, each of said modular optical systems comprising a positive lens, a diaphragm with a hole, and a support tube maintaining said hole at the focal point of the positive lens.

11. An optical detector as claimed in claim 1, which is operable to signal the presence or absence of an object or hole of a small size at a great distance from the detector in the vicinity of the focus of said converging lens.

12. An optical detector as claimed in claim 1, which is operable such that it does not respond to objects located between the detector and the focus of said converging lens.

13. An optical detector as claimed in claim 1, wherein said first optical system comprises a light emitting diode as a light source.

14. An optical detector as claimed in claim 1 further comprising at least one marking optical system for illuminating with visible radiation the focus of said common converging lens.

15. An optical detector as claimed in claim 1 further comprising:

first and second marking optical systems for illuminating with visible radiation the focus of said converging lens associated in common with said first and second optical systems, the optical axis of said first and second marking optical systems being both parallel to the axis of said converging lens and to the optical axis of said first and second optical systems, wherein said first and second marking optical systems each include:

(1) a photo-diode operating in the visible range,
(2) a diaphragm with a centered hole, and
(3) a positive lens having a focal point centered at said hole of said diaphragm, said positive lens sending the image from this centered hole through a parallel marking beam to said converging lens, thereby allowing the focal point of the converging lens to be indicated by superposition of the image of the centered holes of said diaphragms.

16. An optical detector for the detection of very small objects comprising:

(a) a first optical system defining an optical path and operable for transmitting electromagnetic radiation;

(b) a second optical system defining an optical path parallel to an optical path of said first optical system and operable for receiving said electromagnetic radiation after diffusion and reflection by said object; and (c) a converging lens associated in common with said first and second optical systems and arranged such that said optical paths of said first and second optical systems are parallel to and symmetric about the axis of said converging lens on one side thereof, wherein (d) said first optical system further comprises:
(i) means for transmitting said electromagnetic radiation to said converging lens in a parallel beam,
(ii) said means including interchangeable diaphragms each having a hole of a particular size whose image is transmitted by said electromagnetic radiation to the focus of said converging lens, for providing changeable sensitivity for said detector, whereby a desired sensitivity is provided for the detection of corresponding objects of small volume.

17. An optical detector for the detection of very small objects comprising:

(a) a first optical system defining an optical path and being operable for transmitting electromagnetic radiation;

(b) a second optical system defining an optical path parallel to said optical path of said first optical system and being operable for receiving said electromagnetic radiation after diffusion and reflection by an object;

(c) a converging lens associated in common with said first and second optical systems and arranged such that said optical paths of said first and second optical systems are parallel to and symmetrical about the axis of said converging lens on one side thereof; and (d) at least one marking optical system for illuminating the focus of said converging lens.

18. An optical detector as recited in claim 17 wherein said marking optical system comprises two marking optical subsystems having substantially parallel optical paths.

19. An optical detector as recited in claim 17 wherein said marking optical system defines an optical path substantially parallel to said optical paths of said first and second optical systems, and wherein said converging lens is further associated with said marking optical system.

20. An optical detector as recited in claim 17 wherein said marker optical system comprises visible light generating means, a diaphragm having a hole therein and a positive lens having a focal point at said hole, said positive lens transmitting an image focused at said hole to said converging lens, which then forms an image of said hole at the focus of said converging lens.

21. An optical detector as recited in claim 17 wherein said first and second optical systems comprise first and second diaphragms, respectively, having first and second holes, respectively, and first and second lenses, respectively, said first lens collimating the electromagnetic radiation from said first hole and said second lens providing at said second hole an image of the focus of said converging lens.

22. An optical detector as recited in claim 21 wherein said first, second and marking optical system are formed in self-contained modules.

23. An optical detector as recited in claim 22 wherein a plurality of said modules, having coordinated optical characteristics, provide said optical detector with selectable properties.

* * * * *

UNITED STATES PATENT AND TRADEMARK OFFICE
CERTIFICATE OF CORRECTION

PATENT NO. : 4,283,146

DATED : August 11, 1981

INVENTOR(S) : Philippe Roussel

It is certified that error appears in the above—identified patent and that said Letters Patent is hereby corrected as shown below:

Column 8, claim 16, line 9, "said" should read -- an --.

Signed and Sealed this

Thirteenth Day of October 1981

[SEAL]

Attest:

GERALD J. MOSSINGHOFF

Attesting Officer

Commissioner of Patents and Trademarks